US012011418B2

(12) United States Patent
Su

(10) Patent No.: US 12,011,418 B2
(45) Date of Patent: Jun. 18, 2024

(54) FIXING DEVICE FOR NASOGASTRIC TUBE

(71) Applicant: Chien-Chung Su, Taichung (TW)

(72) Inventor: Chien-Chung Su, Taichung (TW)

(*) Notice: Subject to any disclaimer, the term of this patent is extended or adjusted under 35 U.S.C. 154(b) by 302 days.

(21) Appl. No.: 17/471,472

(22) Filed: Sep. 10, 2021

(65) Prior Publication Data

US 2022/0110835 A1    Apr. 14, 2022

(30) Foreign Application Priority Data

Oct. 12, 2020 (TW) .................................. 109135090

(51) Int. Cl.
*A61J 15/00* (2006.01)

(52) U.S. Cl.
CPC ....... *A61J 15/0061* (2013.01); *A61J 15/0003* (2013.01)

(58) Field of Classification Search
CPC ............... A61J 15/0061; A61J 15/0003; A61J 15/0053; A61F 13/126; A61M 2025/0226; A61M 2025/024; A61M 2025/0266; A61M 2025/028; A61M 25/02; A61M 16/0825; A61M 16/0816; A61M 2210/0618

See application file for complete search history.

(56) References Cited

U.S. PATENT DOCUMENTS 5,752,511 A * 5/1998 Simmons .......... A61M 16/0497
                                              128/207.18
2019/0167499 A1* 6/2019 Nahavandi ........... A61G 7/0506

* cited by examiner

*Primary Examiner* — Brandy S Lee
*Assistant Examiner* — Phoebe Anne Staton
(74) *Attorney, Agent, or Firm* — Demian K. Jackson; Jackson IPG PLLC

(57) ABSTRACT

A fixing device of a nasogastric tube contains: an adhesion member, a connection member, and a retainer. The adhesion member includes an adhesive face, a circular column, and an engagement portion. The connection member includes a connecting sheet, a locating post, and a spherical portion. The connecting sheet has a rectangular slot and an annular orifice, such that the annular orifice accommodates the engagement portion of the adhesion member, the rectangular slot slidably receives the circular column of the adhesion member, an end of the connecting sheet proximate to the annular orifice is connected with the locating post, and the other end of the locating post is connected with the spherical portion. The retainer includes a coupling bar and a joining knob. The retainer further includes a clamp section and two press portions. Furthermore, the clamp section has a hollowly circular space defined therein.

6 Claims, 11 Drawing Sheets

FIXING DEVICE FOR NASOGASTRIC TUBE

BACKGROUND OF THE INVENTION

Field of the Invention

The present invention relates to a feeding system, and more particularly to a fixing device of a nasogastric tube.

Description of the Prior Art

With a development of science and technology and an advancement of medical technology, there have been significant breakthroughs and evolutions in a discovery and a treatment of diseases, so it relatively increases a survival rate of injured patients. When patients are unable to eat on their own because of injury or aging, medical personnel or family members are fed via a nasogastric tube feeder. In other words, by using intubation, an amount of residual food in the stomach and gastric acid detection, infusion of warm water to warm the stomach and intestines, infusion of nutrient solution (such as milk) to supply the patients with the required nutrition And infusion of drugs to provide therapeutic effects, etc.

At present, the nasogastric tube in the prior art is a medical device used to introduce fluid into a patient's body or remove it from the body. The nasogastric tube is provided with a connection structure for introducing or removing the fluid on the outer end of the human body. However, when passing through the nostrils to the inside of the stomach, a section is often exposed, thus when the patient turns over or performs any nursing measures, the nasogastric tube is accidentally pulled, which may easily cause slippage and affect the patient. Most of the nasogastric tube not only affects the normal life of patients, but also easily increases patient injuries and medical accidents, thus interfering with patients' actions to cause inconvenience and danger.

A conventional method for fixing the nasogastric tube with air-permeable tape contains: taking a piece of air-permeable tape, then sticking one end of the tape along the bridge of the nose, and finally sticking the other end of the tape around the nasogastric tube to fixing the nasogastric tube completely.

However, such method will cause following inconveniences:
1) It is necessary to cut an air-permeable tape to have troublesome operation.
2) Because the air-permeable tape surrounds and sticks the nasal cavity so as to be a focus of the nasogastric tube, thus having nasal ulcers and infections.
3) The nasogastric tube is easy to pull during the tearing process, which aggravates the patient's discomfort.
4) The air-permeable tapes are wound and bonded into a bundle, which makes a non-adhesive surface of the tape easy to have adhesive residue and stickiness. Therefore, it is not only easy to produce dirt, but also has the doubt of germ infection.

The present invention has arisen to mitigate and/or obviate the afore-described disadvantages.

SUMMARY OF THE INVENTION

The primary object of the present invention is to provide a fixing device of a nasogastric tube which is capable of adjusting a nasogastric tube freely to enhance a using comfort, and the fixing device does not force an inner wall of a patient's nostril by using a joining knob and a coupling bar of a retainer after a period of using time, thus avoiding a sore of the nostril.

Another object of the present invention is to provide a fixing device of a nasogastric tube which is configured to connect an adhesion member, a connection member, and a retainer together so that the nasogastric tube is fixed onto the patient easily.

To obtain above-mentioned aspect, a fixing device of a nasogastric tube provided by the present invention contains: an adhesion member, a connection member, and a retainer.

An end of the adhesion member is adhered on a patient's nose bridge, and the other end of the adhesion member is movably connected with the connection member, wherein an end of the connection member proximate to the adhesion member is rotatably connected with the retainer, and the retainer is configured to fix the nasogastric tube on the patient and to adjust a position of the nasogastric tube in the patient's nostril freely.

DETAILED DESCRIPTION OF THE PREFERRED EMBODIMENTS

Figure 1:
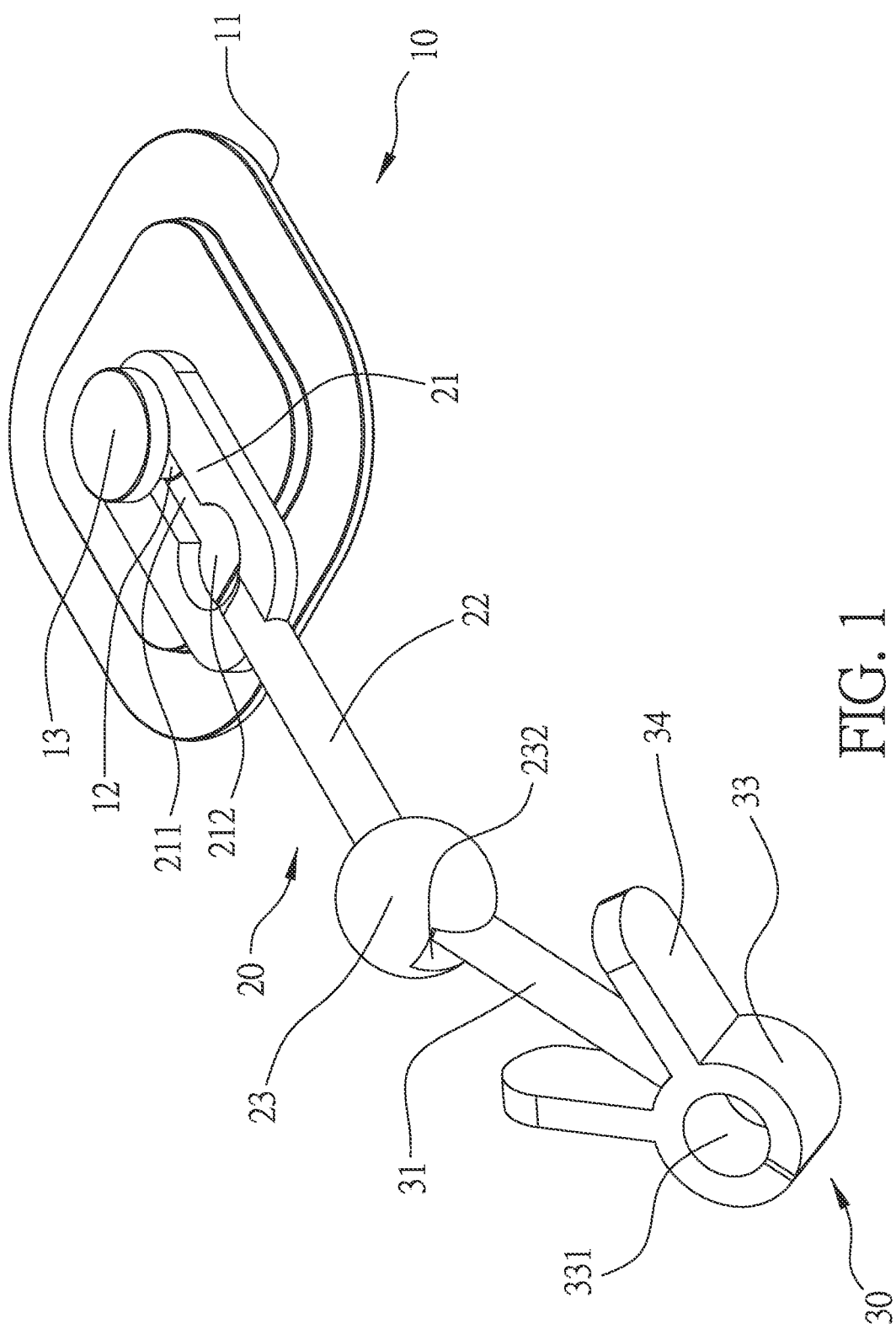
FIG. 1 is a perspective view showing the assembly of a fixing device of a nasogastric tube according to a preferred embodiment of the present invention.
Figure 2:
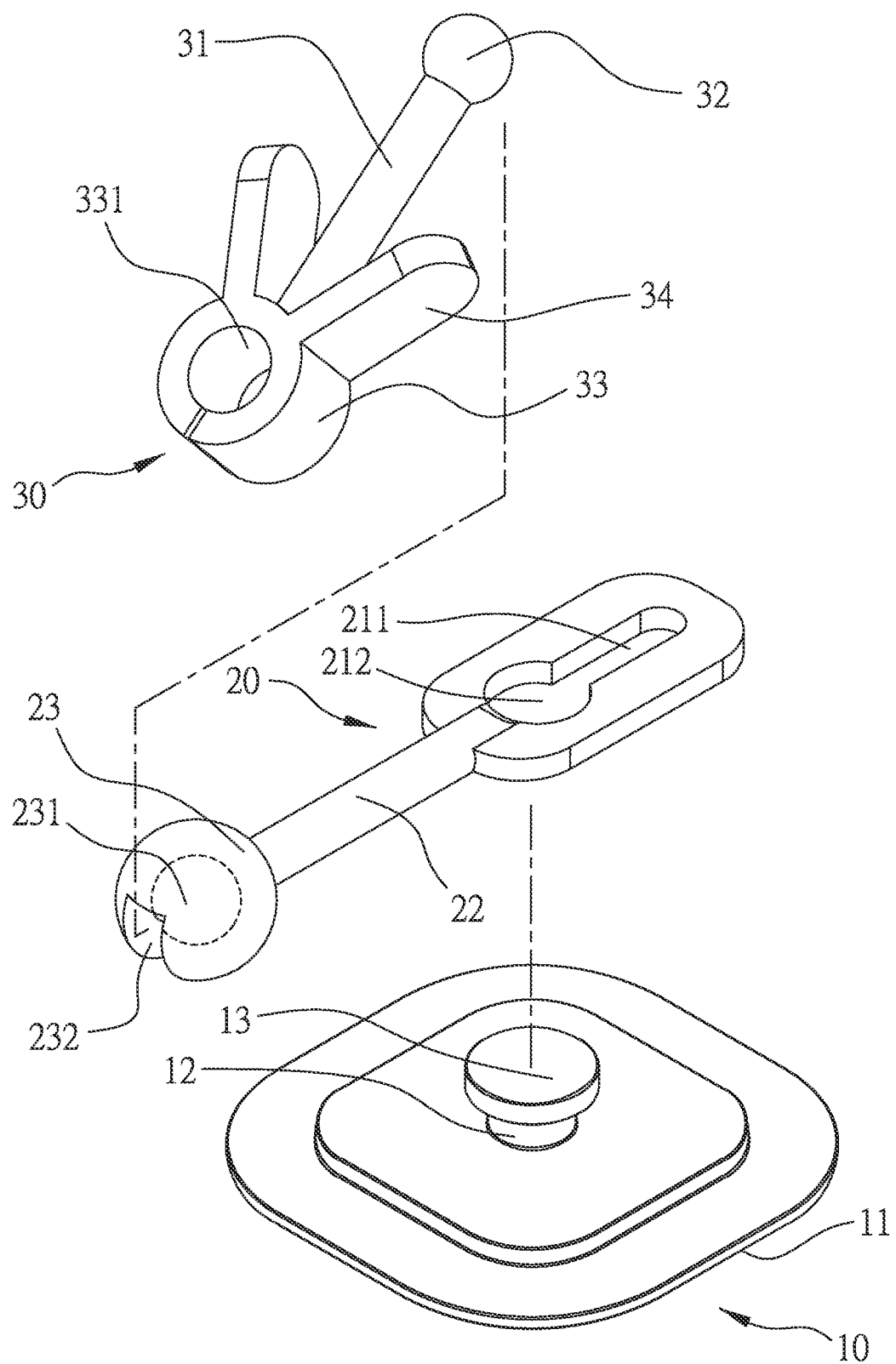
FIG. 2 is a perspective view showing the exploded components of the fixing device of the nasogastric tube according to the preferred embodiment of the present invention.
Figure 3:
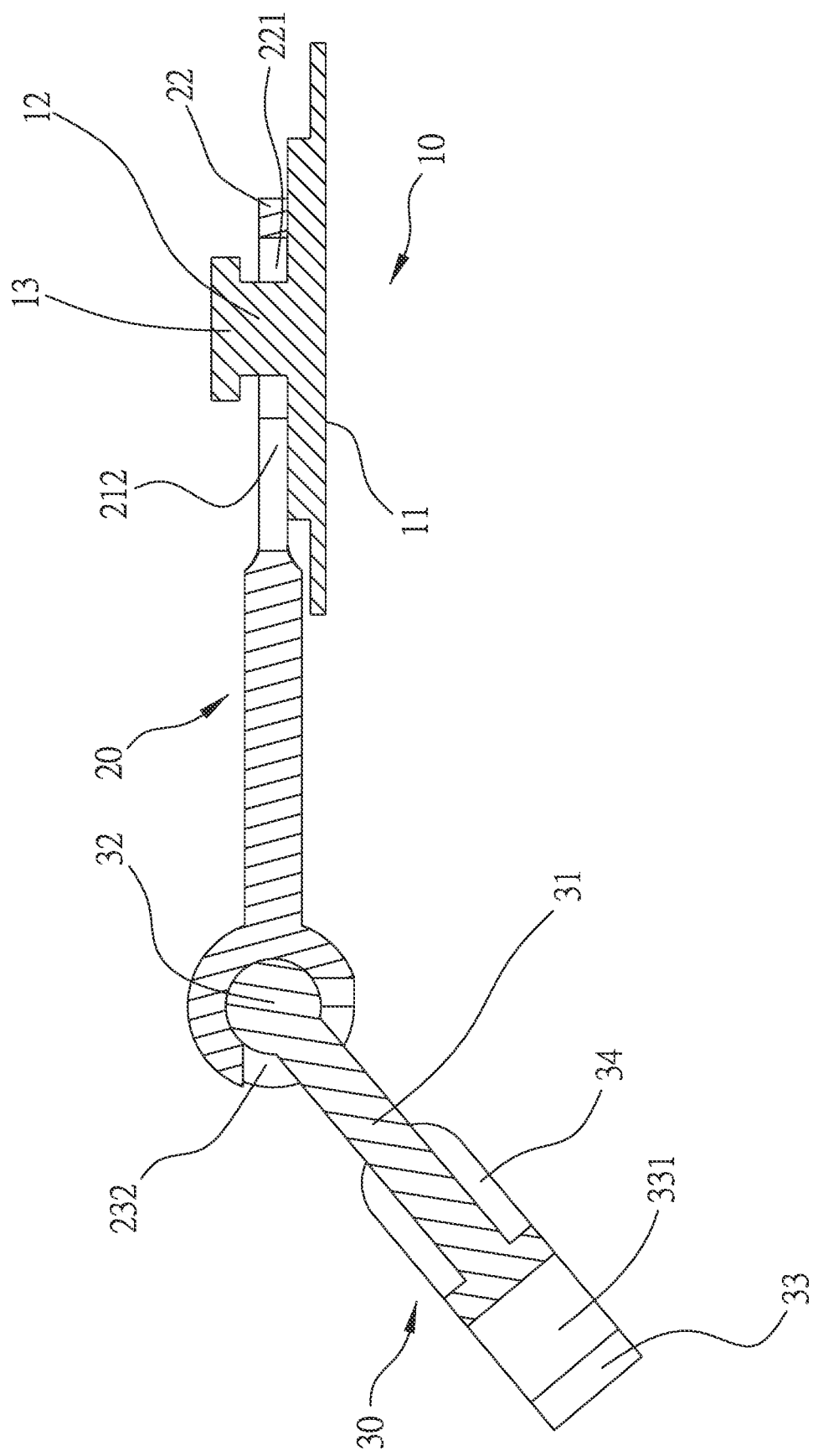
FIG. 3 is a cross sectional view showing the assembly of the fixing device of the nasogastric tube according to the preferred embodiment of the present invention.
Figure 4:
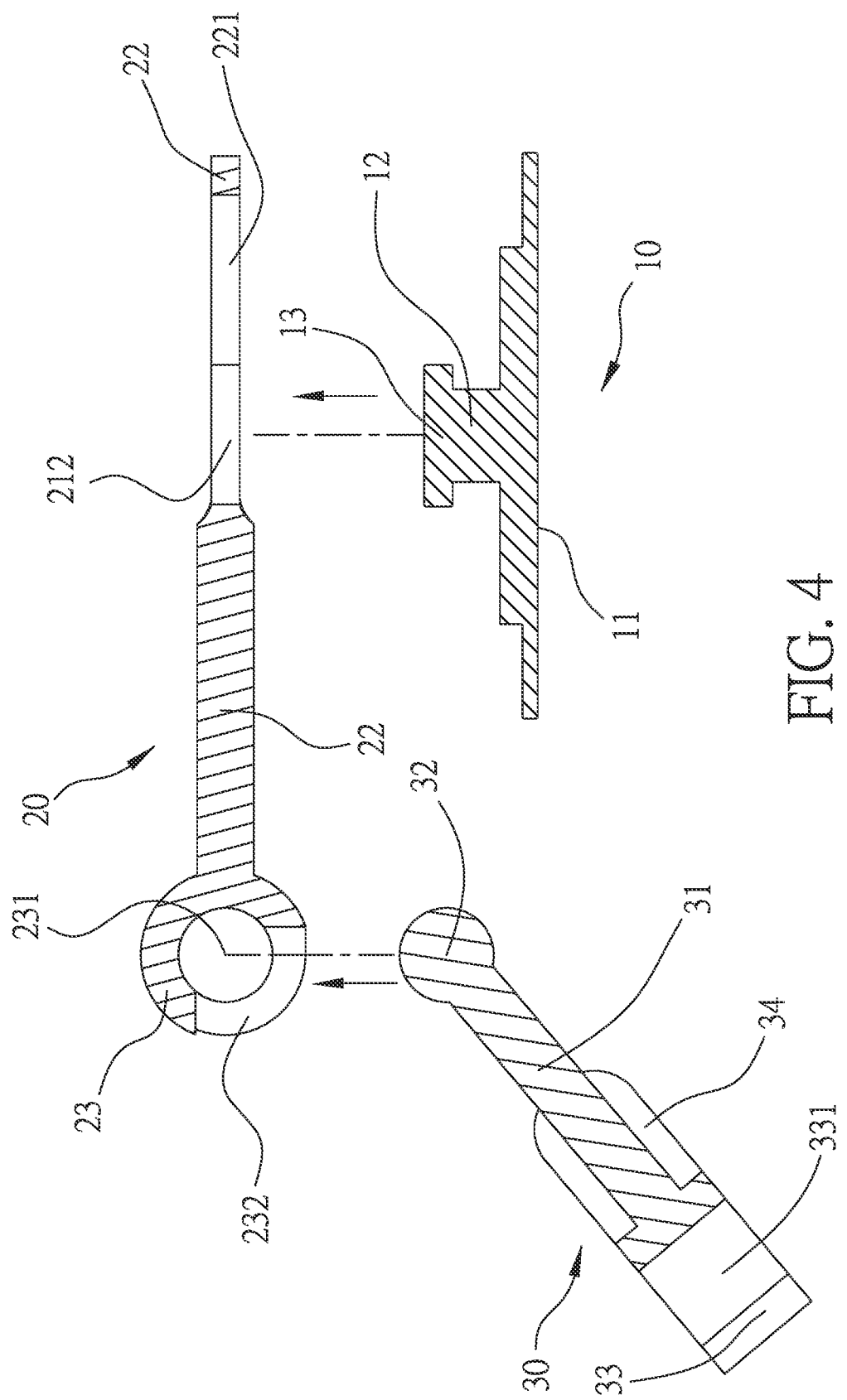
FIG. 4 is a cross sectional view showing the operation of the fixing device of the nasogastric tube according to the preferred embodiment of the present invention.
Figure 5:
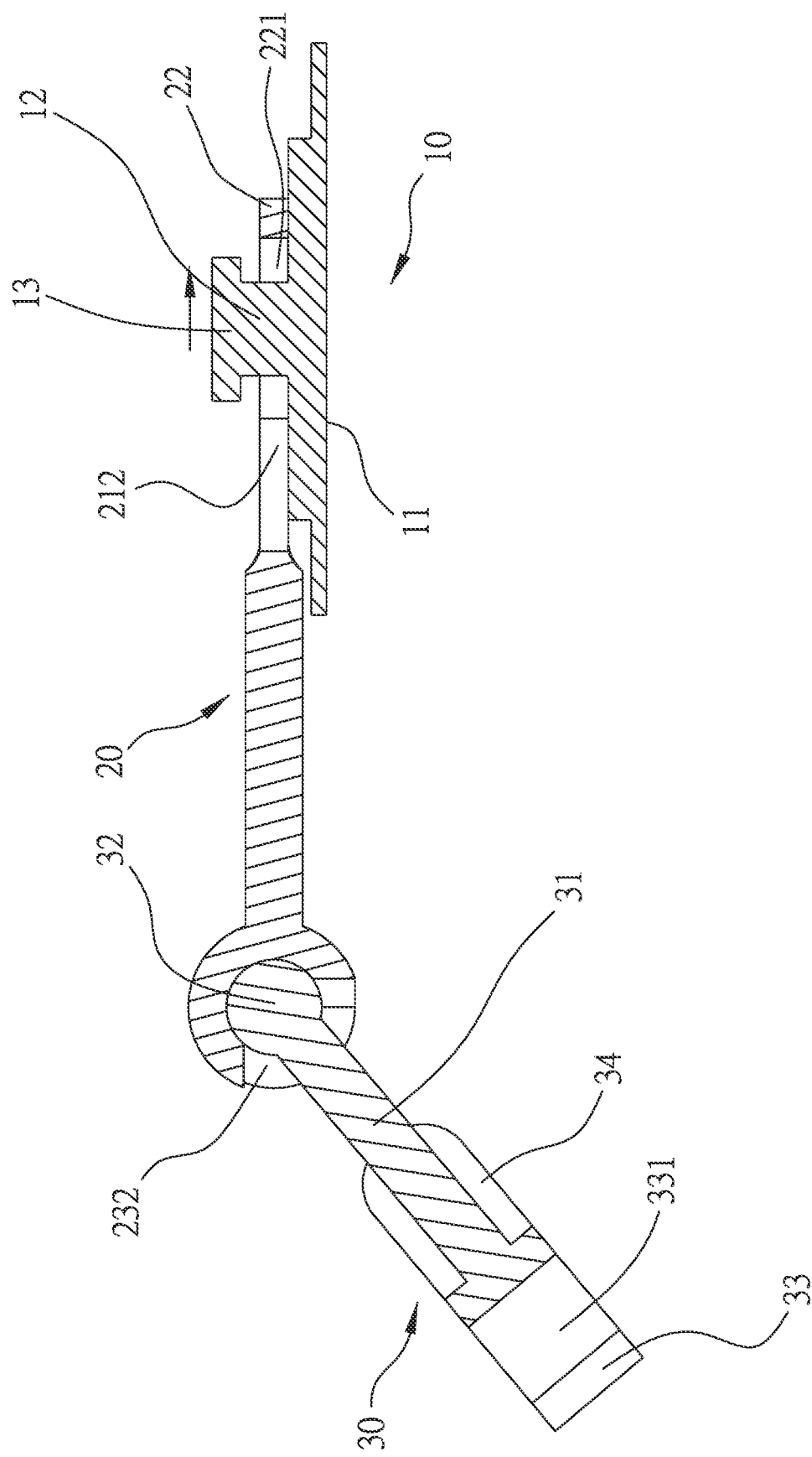
FIG. 5 is another cross sectional view showing the operation of the fixing device of the nasogastric tube according to the preferred embodiment of the present invention.
Figure 6:
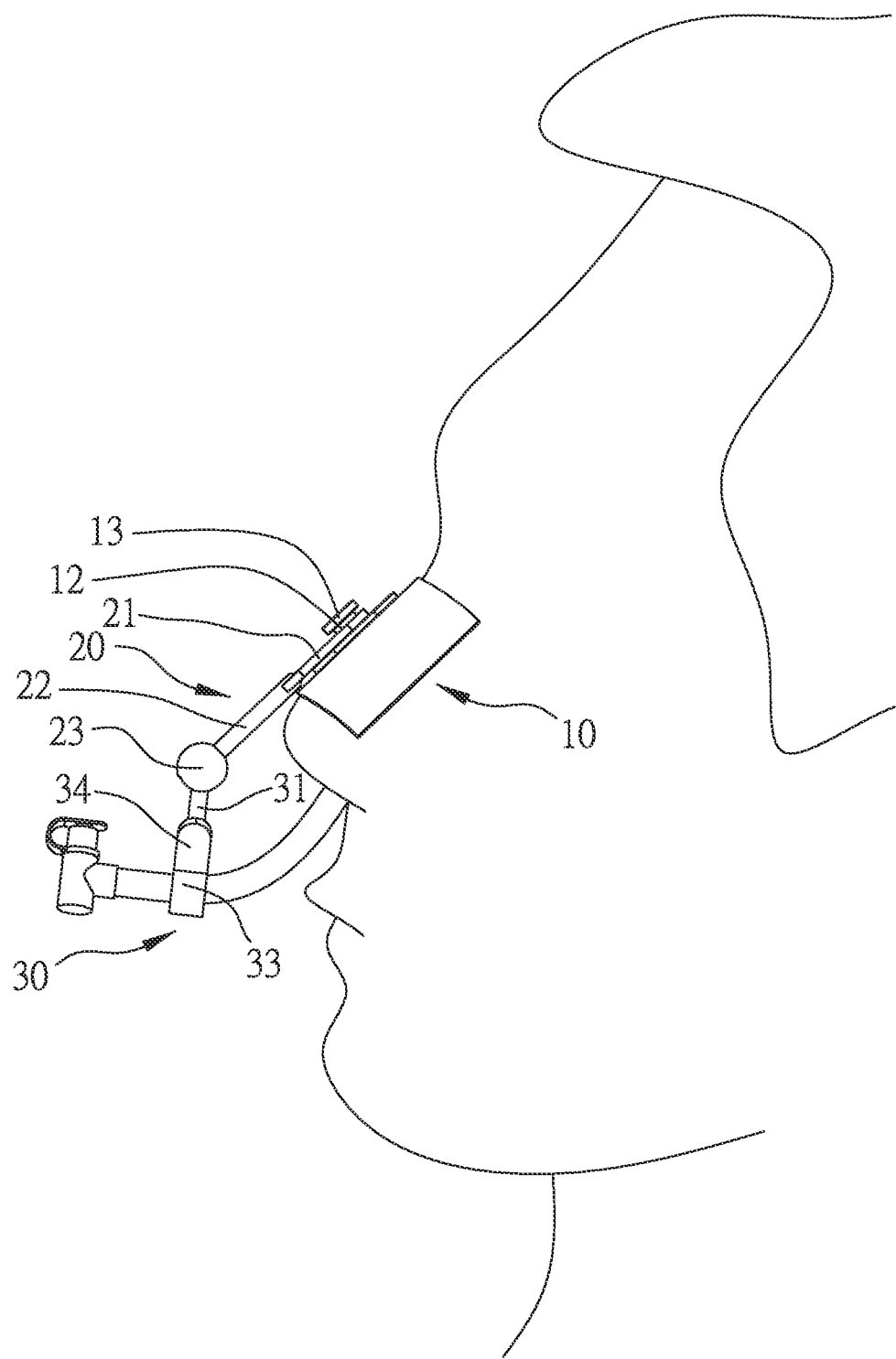
FIG. 6 is a side plan view showing the application of the fixing device of the nasogastric tube according to the preferred embodiment of the present invention.
Figure 7:
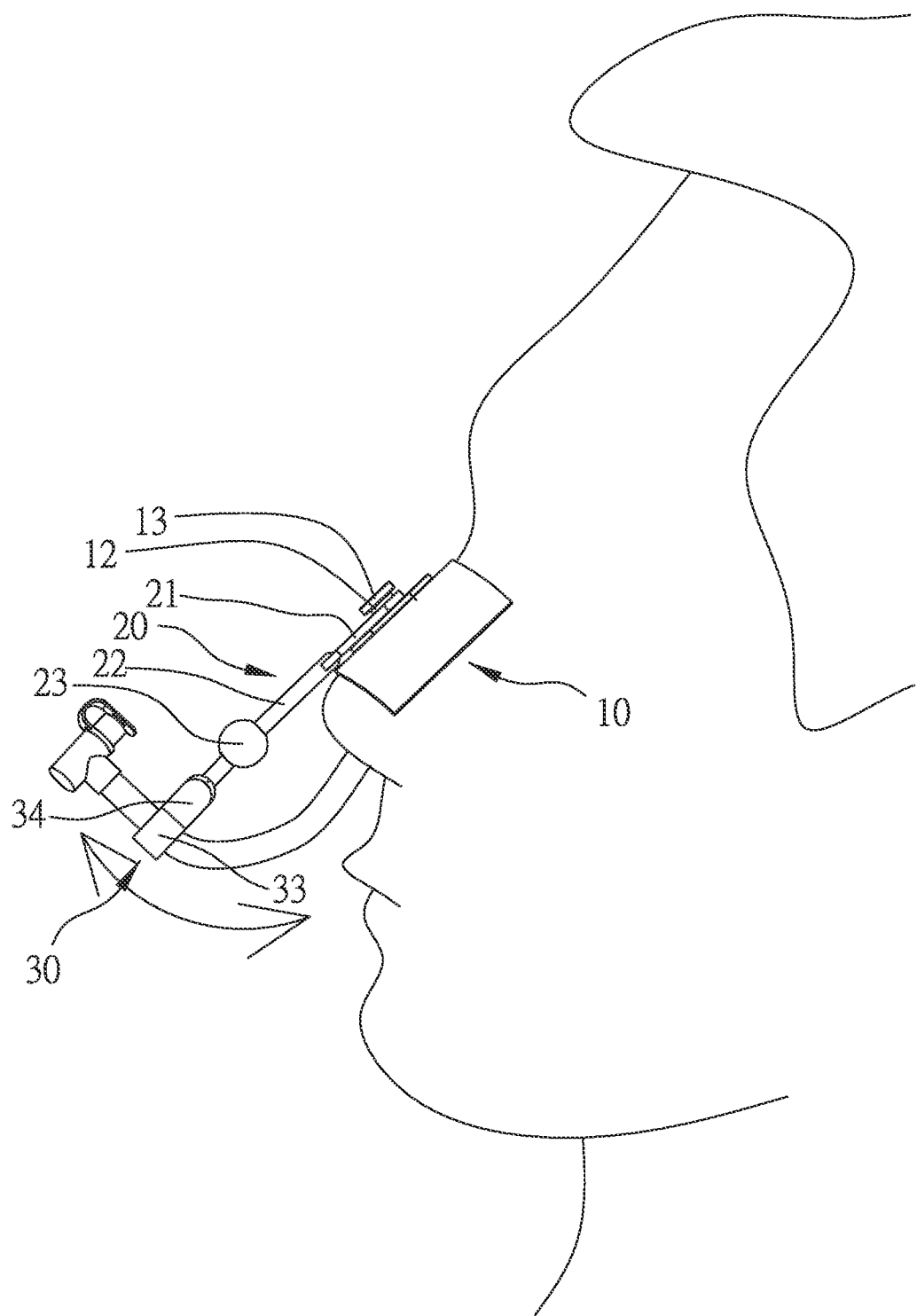
FIG. 7 is another side plan view showing the application of the fixing device of the nasogastric tube according to the preferred embodiment of the present invention.
Figure 8:
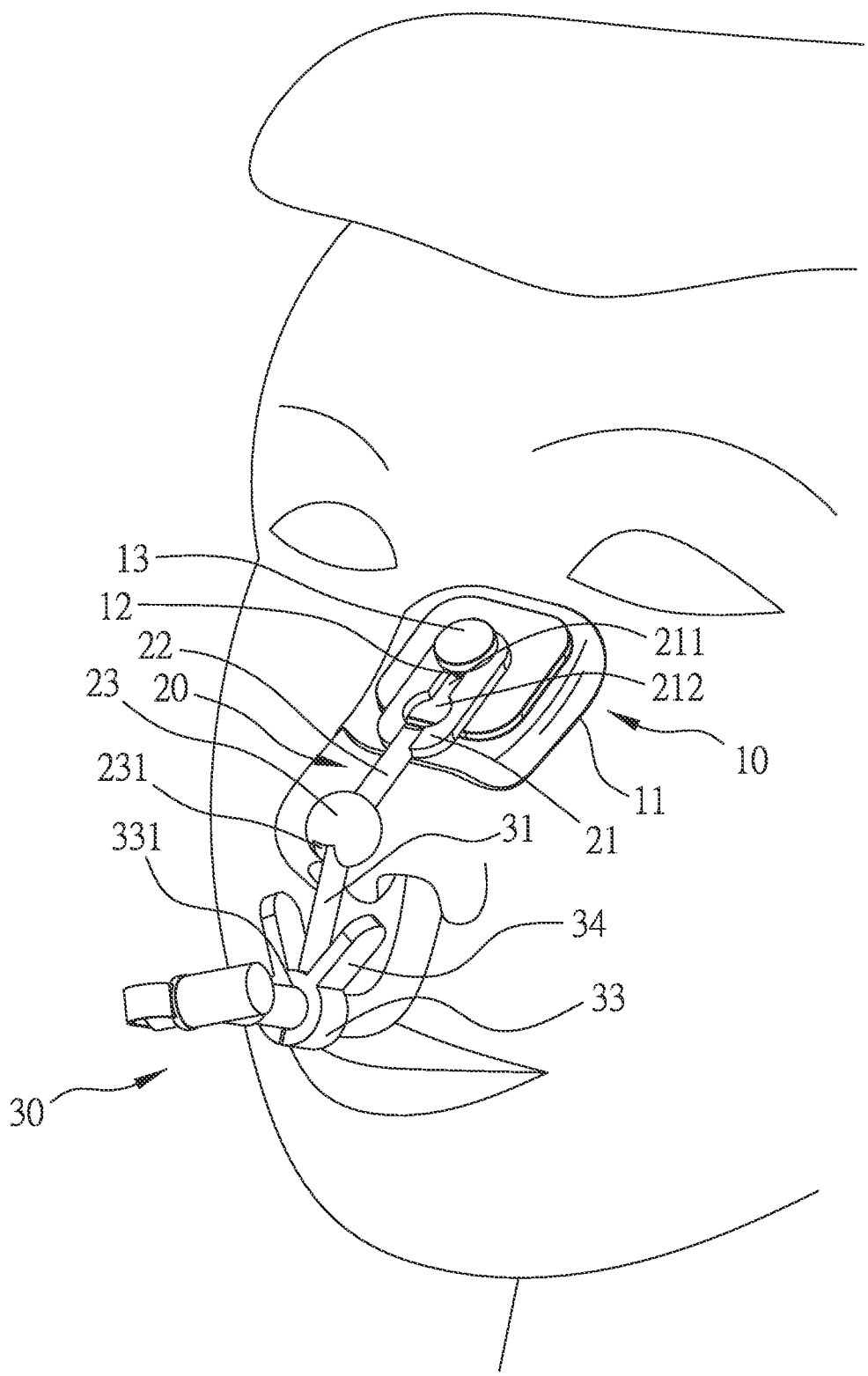
FIG. 8 is a perspective view showing the application of the fixing device of the nasogastric tube according to the preferred embodiment of the present invention.
Figure 9:
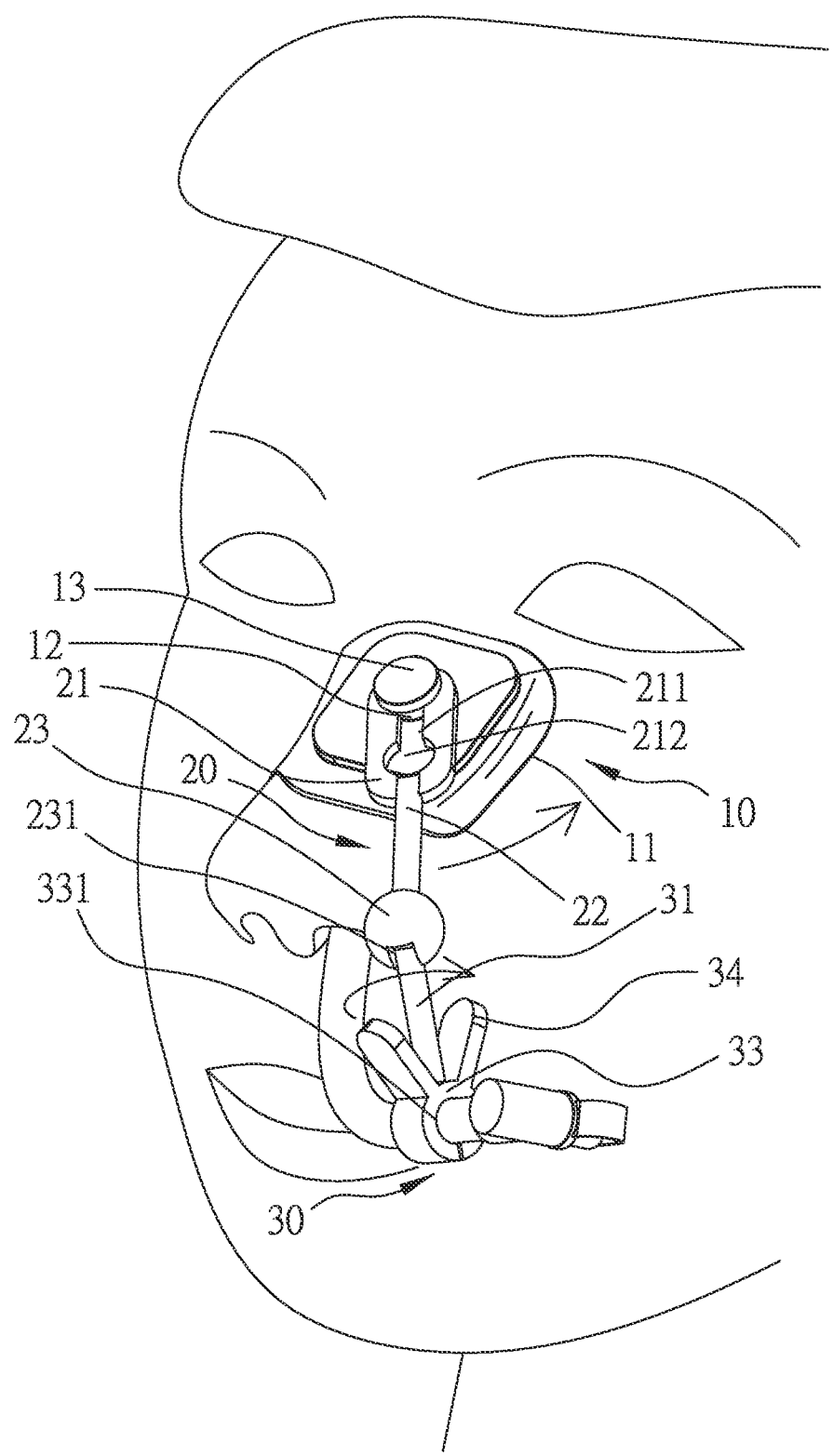
FIG. 9 is another perspective view showing the application of the fixing device of the nasogastric tube according to the preferred embodiment of the present invention.

The present invention will be clearer from the following description when viewed together with the accompanying drawings, which show, for purpose of illustrations only, a preferred embodiment in accordance with the present invention.

With reference to FIGS. 1-5, a fixing device of a nasogastric tube according to a preferred embodiment of the present invention comprises:

an adhesion member 10 formed in a square sheet shape and including an adhesive face 11 made of silicone rubber, a circular column 12 formed a cylindrical shape, and an engagement portion 13 formed in a circular sheet shape, wherein the adhesive face 11 is repeatedly adhered on a patient's nose bridge, the adhesion member 10 has the circular column 12 and the engagement portion 13 which are opposite to the adhesive face 11, and a diameter of the circular column 12 is less than a diameter of the engagement portion 13;

a connection member 20 formed in a key shape and including a connecting sheet 21 which is oval and is one-piece formed with the connection member 20, a locating post 22 which is circular, and a spherical portion 23, wherein the connecting sheet 21, the locating post 22, and the spherical portion 23 are one-piece formed, and the connecting sheet 21 has a rectangular slot 211 defined at a center thereof and an annular orifice 212 formed on an end of the connecting sheet 21 and communicating with the rectangular slot 211, such that the annular orifice 212 accommodates the engagement portion 13 of the adhesion member 10, the rectangular slot 211 slidably receives the circular column 12 of the adhesion member 10, an end of the connecting sheet 21 proximate to the annular orifice 212 is connected with the locating post 22, and the other end of the locating post 22 is connected with the spherical portion 23, wherein the spherical portion 23 has a circular recess 231 defined therein, and the circular recess 231 of the spherical portion 23 has a cutout 232 facing to a free end of the spherical portion 23; and a retainer 30 formed in a pendulum shape and including a coupling bar 31 which is a round rod, a joining knob 32 formed on an end of the coupling bar 31 and rotatably accommodated in the circular recess 231 of the spherical portion 23, wherein the retainer 30 further includes a clamp section 33 which is C-shaped and formed on an end of the retainer 30 away from the joining knob 32, two press portions 34 extending to the coupling bar 31, wherein a respective press portion 34 is formed in an oval sheet shape, and the clamp section 33 has a hollowly circular space 331 defined therein, wherein the coupling bar 31, the clamp section 33, and the two press portions 34 are one-piece formed.

Referring to FIGS. 6-9, in operation of the fixing device of the nasogastric tube, the adhesive face 11 of the adhesion member 10 is adhered on the patient's nose bridge, the annular orifice 212 of the retainer 30 is fitted with the circular column 12 and the engagement portion 13 of the adhesion member 10, and the rectangular slot 211 slidably accommodates the circular column 12 of the adhesion member 10, the circular recess 231 of the spherical portion 23 of the connection member 20 rotatably receives the joining knob 32 of the retainer 30, wherein a user presses the two press portions 34 to the coupling bar 31 with a thumb and an index finger by using the joining knob 32 and the coupling bar 31 so that the hollowly circular space 331 clamps the nasogastric tube based on a size of the nasogastric tube after opening the clamp section 33, and the nasogastric tube is moved adjustably in the patient's nostril by ways of the joining knob 32 and the coupling bar 31 of the retainer 30.

Figure 10:
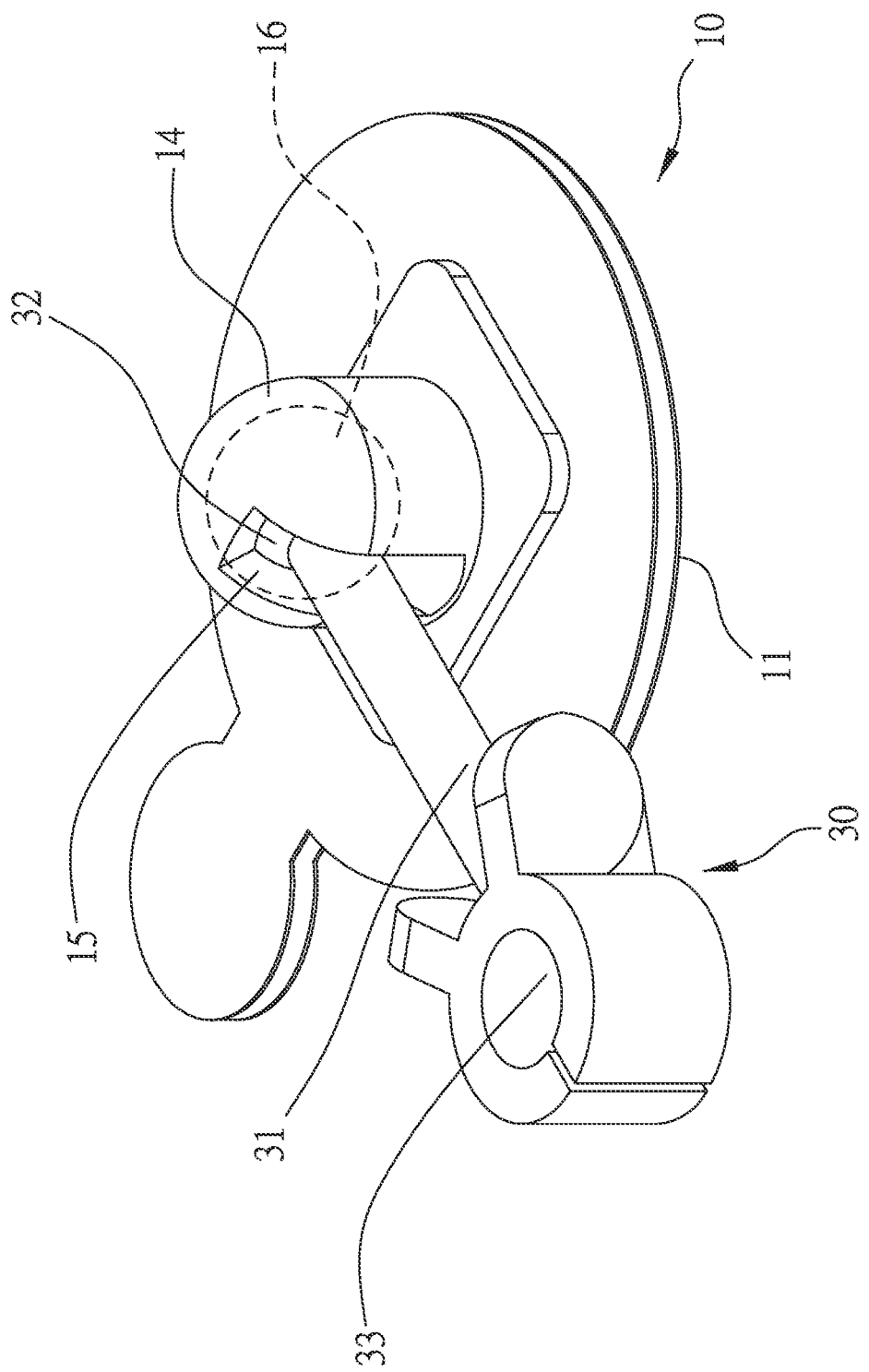
FIG. 10 is also another perspective view showing the application of the fixing device of the nasogastric tube according to the preferred embodiment of the present invention.
Figure 11:
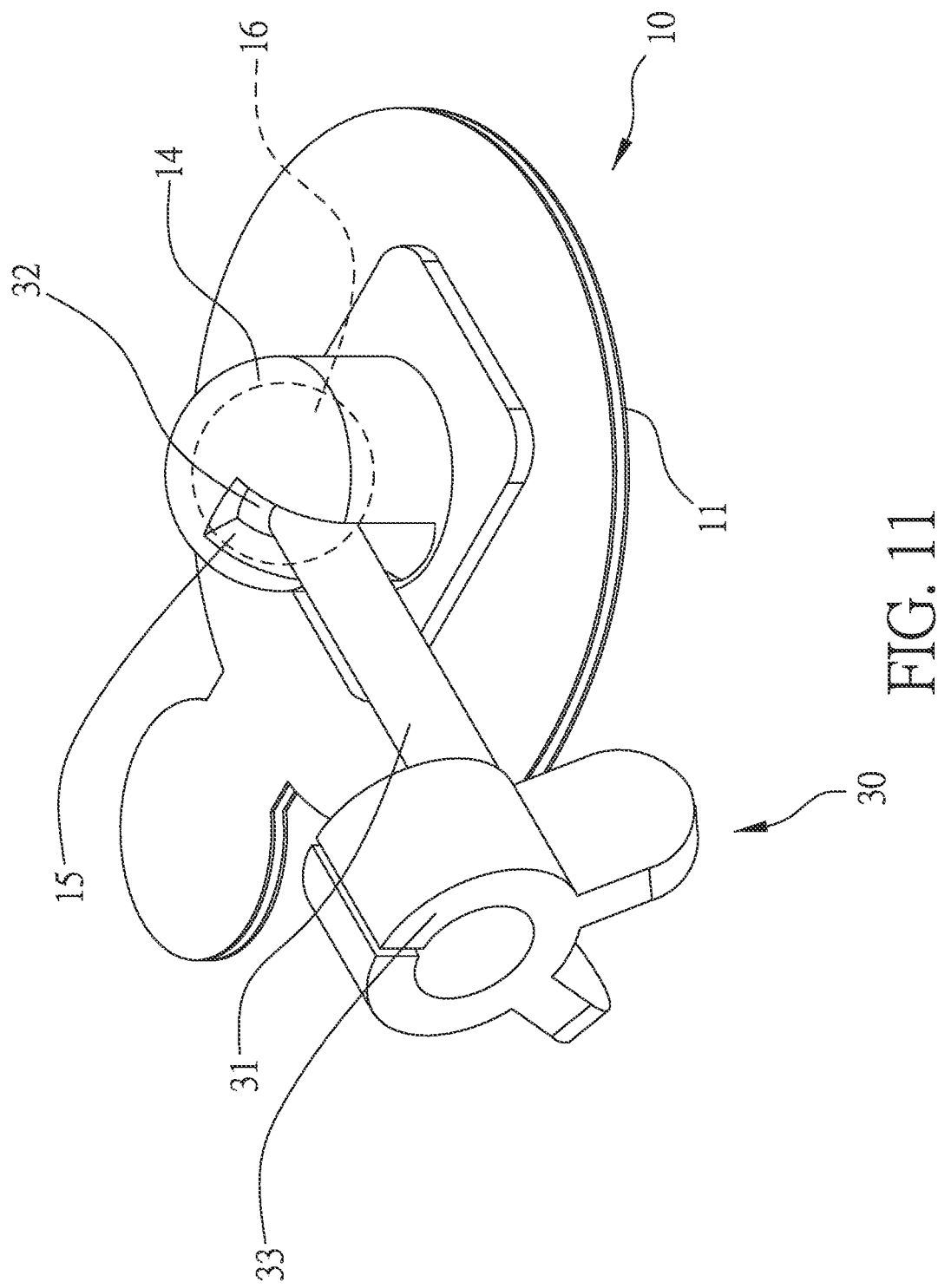
FIG. 11 is still another perspective view showing the application of the fixing device of the nasogastric tube according to the preferred embodiment of the present invention.

As shown in FIGS. 10 and 11, the fixing device of the nasogastric tube is applicable after a thoracic and abdominal surgery, wherein the fixing device of the nasogastric tube comprises the adhesion member 10 formed in a rectangle shape, and the adhesion member 10 includes a semicircular protrusion 14 which is like a bullet, a cutting groove 15 defined on a side of the semicircular protrusion 14, a hollowly circular orifice 16 defined in the cutting groove 15 and configured to rotatably receive the joining knob 32 of the retainer 30, such that the joining knob 32 rotates the adhesion member 10 in the hollowly circular orifice 16. The adhesion member 10 includes an adhesive face 11 formed on an end thereof and adhered on the patient's chest and abdomen, wherein the user presses the two press portions 34 to the coupling bar 31 with the thumb and the index finger by using the joining knob 32 and the coupling bar 31 so that the hollowly circular space 331 clamps the nasogastric tube based on a size of the nasogastric tube after opening the clamp section 33, and the nasogastric tube is moved adjustably on the patient's chest and abdomen by ways of the joining knob 32 and the coupling bar 31 of the retainer 30.

Thereby, the fixing device of the nasogastric tube contains advantages as follows:

1. The fixing device is configured to connect the adhesion member 10, the connection member 20, and the retainer 30 so that the nasogastric tube is fixed onto the patient easily.
2. The nasogastric tube can be capable to adjust the position freely by using the joining knob 32 and the coupling bar 31 of the retainer 30 after a period of using time, thus increasing the comfortability.
3. The nasogastric tube does not force an inner wall of the patient's nostril by using the joining knob 32 and the coupling bar 31 of the retainer 30 after a period of using time, thus avoiding a sore of the nostril.

While various embodiments in accordance with the present invention have been shown and described, it is clear to those skilled in the art that further embodiments may be made without departing from the scope of the present invention.

What is claimed is:

1. A fixing device of a nasogastric tube comprising:
an adhesion member including an adhesive face, a circular column, and an engagement portion, wherein the adhesive face is configured to be adhered on a patient's nose bridge, the circular column and the engagement portion are opposite to the adhesive face, and a diameter of the circular column is less than a diameter of the engagement portion;

a connection member including a connecting sheet, a locating post, and a spherical portion, wherein the connecting sheet has a rectangular slot defined at a center thereof and an annular orifice formed on an end of the connecting sheet and communicating with the rectangular slot, such that the annular orifice accommodates the engagement portion of the adhesion member, the rectangular slot slidably receives the circular column of the adhesion member, an end of the connecting sheet proximate to the annular orifice is connected with a first end of the locating post, and a second end of the locating post is connected with the spherical portion, wherein the spherical portion has a circular recess defined therein, and the circular recess of the spherical portion has a cutout facing to a free end of the spherical portion; and a retainer including a coupling bar, and a joining knob formed on an end of the coupling bar and rotatably accommodated in the circular recess of the spherical portion, wherein the retainer further includes a clamp section formed on an end of the retainer away from the joining knob, two press portions extending to the coupling bar, wherein the clamp section has a hollowly circular space defined therein.

2. The fixing device of the nasogastric tube as claimed in claim 1, wherein the adhesion member is formed in a square sheet shape, and the adhesive face is made of silicone rubber, wherein the circular column is formed in a cylindrical shape, and the engagement portion is formed in a circular sheet shape.

3. The fixing device of the nasogastric tube as claimed in claim 1, wherein the connecting sheet is oval, and the locating post is circular, wherein the connecting sheet, the locating post, and the spherical portion are one-piece formed.

4. The fixing device of the nasogastric tube as claimed in claim 1, wherein the coupling bar, the clamp section, and the two press portions are one-piece formed.

5. The fixing device of the nasogastric tube as claimed in claim 1, wherein the coupling bar is a round rod, and the clamp section is C-shaped.

6. The fixing device of the nasogastric tube as claimed in claim 1, wherein a respective press portion of the two press portions is formed in an oval sheet shape.

\* \* \* \* \*